United States Patent [19]
Graupner

[11] Patent Number: 5,821,115
[45] Date of Patent: Oct. 13, 1998

[54] CARTRIDGE FOR TREATING SAMPLES FOR HISTOLOGICAL EXAMINATION, IN PARTICULAR FOR PREPARING SLICES

[75] Inventor: Dag Graupner, Eppelheim, Germany

[73] Assignee: Leica Instruments GmbH, Nussloch, Germany

[21] Appl. No.: 619,511

[22] PCT Filed: Sep. 28, 1994

[86] PCT No.: PCT/DE94/01123

§ 371 Date: Mar. 29, 1996

§ 102(e) Date: Mar. 29, 1996

[87] PCT Pub. No.: WO95/09352

PCT Pub. Date: Apr. 6, 1995

[30] Foreign Application Priority Data

Sep. 29, 1993 [DE] Germany .......................... 43 33 118.1

[51] Int. Cl.⁶ .................................................. C12M 1/16
[52] U.S. Cl. .................................. 435/283.1; 435/307.1; 422/99; 422/102
[58] Field of Search ................................ 435/40.5, 40.52, 435/284.1, 307.1, 809, 283.1; 422/99, 104, 102, 292, 300; 220/676, 306, 373, 607, 485, 367.1; 118/500; 425/117

[56] References Cited

U.S. PATENT DOCUMENTS

| 3,674,396 | 7/1972 | McCormick | 422/102 |
| 4,220,252 | 9/1980 | Beall et al. | 220/307 |
| 4,421,246 | 12/1983 | Schultz et al. | 220/307 |
| 5,080,869 | 1/1992 | Schultz et al. | 220/307 |
| 5,127,537 | 7/1992 | Graham | 220/339 |

FOREIGN PATENT DOCUMENTS

| 0 471 534 | 2/1992 | European Pat. Off. . |
| G 93 02 996.9 | 3/1993 | Germany . |

*Primary Examiner*—William H. Beisner
*Attorney, Agent, or Firm*—Foley & Lardner

[57] ABSTRACT

A cartridge for treating samples in liquids and for preparing samples to be cut into slices for microscope examination includes a bottom part, lateral parts, and a detachably secured lid part. The bottom part and lid part each have a plurality of slot-shaped openings, and the lateral parts are free of openings. The slot-shaped openings in the bottom part and in the lid part are arranged at an oblique angle relative to the top surface of the bottom part and the top surface of the lid part, respectively.

4 Claims, 2 Drawing Sheets

CARTRIDGE FOR TREATING SAMPLES FOR HISTOLOGICAL EXAMINATION, IN PARTICULAR FOR PREPARING SLICES

BACKGROUND OF THE INVENTION

The invention relates to a cartridge for treating samples in liquids, in particular for a subsequent embedding in histological paraffin. This embedding is used for preparing samples to be cut into slices for microscope examination.

The standard method which is customary today involves treating the sample by means of multiple chemical fixing in buffered aldehyde and/or formalin solutions. The aim of this is to ensure that the sample is dewatered. After the dewatering, paraffin is infiltrated into the sample for the purpose of stabilization.

For chemical fixing and dewatering, the sample is introduced into a cartridge provided with openings. Individual cartridges or a plurality of cartridges are treated in a special container—histoprocessor—with the appropriate reagents. The treatment is preferably carried out by constantly pumping the appropriate liquid around in the container. The movement of the liquid in the container is intended to shorten the duration of treatment of the sample and at the same time to achieve a good depth of penetration of the liquid into the sample.

It has been found, when treating the samples, that the duration of treatment and the depth of penetration can be optimized if the liquids do not flow evenly across the surface of the sample, and if instead swirling occurs on the surface of the sample.

Known cartridge systems are described in U.S. Pat. No. 3,674,396, U.S. Pat. No. 4,220,252 and U.S. Pat. No. 4,421,246, for example. These cartridges have a rectangular main body with a bottom and side walls, with openings in the form of bores or slots being provided in the bottom and/or in the side walls. The cartridges are in some cases designed so that they can be stacked on top of one another, and they are closed off by a lid which is likewise provided with openings. The cartridges described in the abovementioned documents have proven themselves in practice only to a qualified extent, since the liquid being pumped around flows past the samples as a continuous stream. As a result of this, not only does a longer duration of treatment occur, but also a relatively poor depth of penetration of the liquid into the sample. In the case of relatively large samples, the degree of chemical treatment may even be completely inadequate, as a result of which the sample is unserviceable for the subsequent slicing.

A cartridge which optimizes the duration of treatment and the depth of penetration is known from EP 0 471 534 A2 and the corresponding U.S. Pat. No. 5,080,869.

In both documents, a stackable cartridge system is described in which slot-shaped openings are arranged in the bottom and in the side walls of a rectangular container. The openings in the side walls are arranged obliquely in relation to the respective walls. By means of this measure, a swirling of the liquid on the surface of the sample and consequently an optimized duration of treatment and depth of penetration are achieved. A lid with slots is provided for closing the cartridge, the openings in the bottom and lid being arranged in parallel above one another and extending perpendicularly through the lid surface and bottom surface.

Since cartridges of this type have very small dimensions (e.g. 2.5 cm * 3.5 cm) and are preferably made of plastic, it has been found in practice that precision manufacture of such cartridges is made very difficult by the large number of openings and is associated with a large amount of waste material. It has also been found, during practical application of the cartridge, that as a result of the large number of openings provided in the bottom, lid, and side walls, the cartridge has become unstable with respect to mechanical deformations. Thus, in addition to the limited stackability, difficulties also arise when closing the cartridge with the plastic lid.

SUMMARY OF THE INVENTION

It is therefore the object of the present invention, starting from the known prior art, to guarantee the optimized flow of the respective reagents inside the cartridge and in so doing to ensure, in addition to simplified manufacture, the mechanical stability of the cartridge.

According to the invention, this object maybe achieved by a cartridge for treating liquids and for preparing samples to be cut into slices for microscope examination. The cartridge has a bottom part and lateral parts formed integrally thereon. The cartridge also has a detachably secured lid part. The bottom part and lid part have a plurality of slot-shaped openings. The lateral parts are designed as a closed unit. The slot-shaped openings in the bottom part and in the lid part are arranged at an oblique angle relative to the top surfaces of the bottom part and the lid part. Advantageous further embodiments of the invention include arranging the openings in the bottom part and the openings in the lid part in the flow direction in alignment one above the other or, alternatively, arranging these openings in the flow direction offset in relation to one another. The through-angle of the openings in the bottom part may differ from the through-angle of the openings in the lid part. In addition, the longitudinal direction of the openings in the bottom part or the lid part may be oriented in relation to the lateral parts at an oblique angle. Also, the bottom part may be designed together with the lateral parts as a one-piece injection-molded plastic part.

DESCRIPTION OF THE DRAWINGS

The cartridge according to the invention is explained in greater detail hereinafter on the basis of several illustrative embodiments, and with reference to the diagrammatic representations in the drawing, in which.

DETAILED DESCRIPTION OF THE PREFERRED EMBODIMENT

Figure 1:
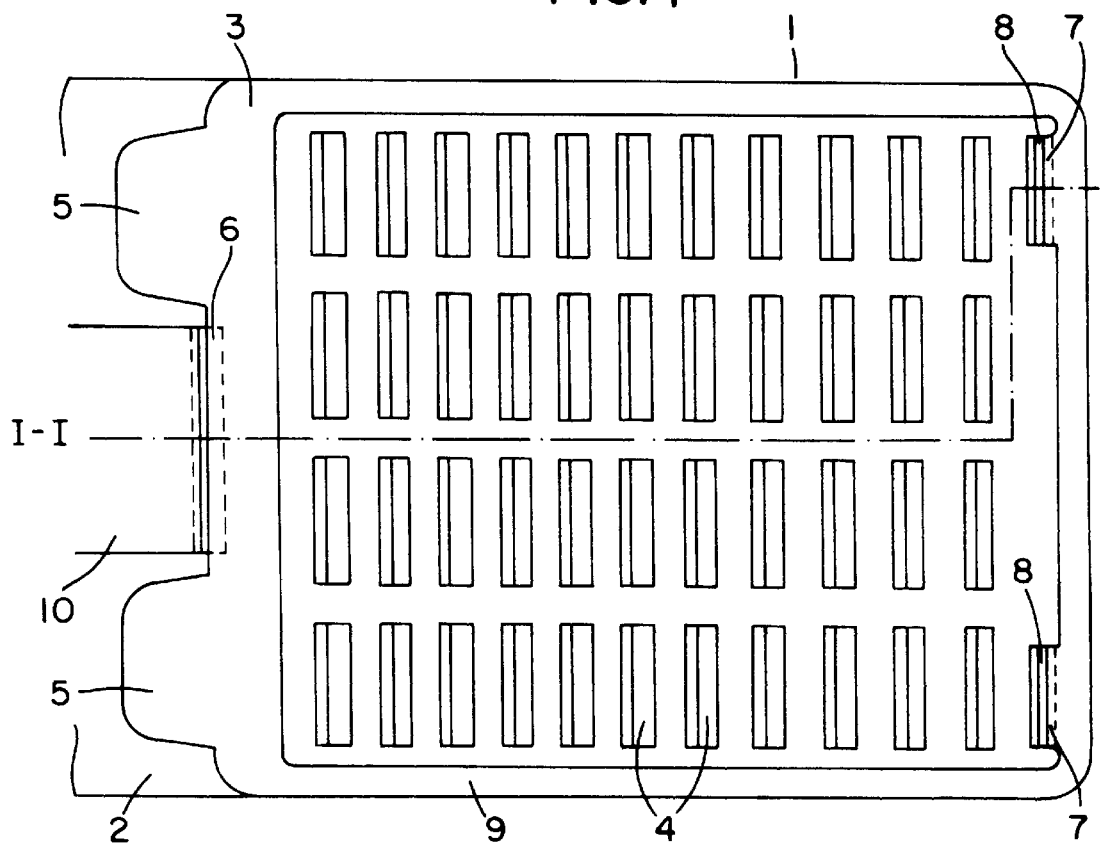
FIG. 1 shows the closed cartridge in a plan view.

FIG. 1 shows a plan view of a closed cartridge 1 with a bottom part 2, lateral parts 9, and a lid part 3. The bottom part 2 and the lateral parts 9 are designed as a one-piece injection-molded plastic part. A plurality of slot-shaped openings 4 are provided in each case in the bottom part 2 and lid part 3.

The lid part 3 is connected detachably to the lateral parts 9. For this purpose, the lid part 3 has two closure hooks 7 and one closure hook 6, which engage in hooks 8 and 10, respectively, in the bottom part 2. By means of this connection, the cartridge 1 is closed off against the liquid flowing out at the sides. For better handling of the cartridge 1, two tabs 5 are integrally formed on the lid part 3.

Figure 2:
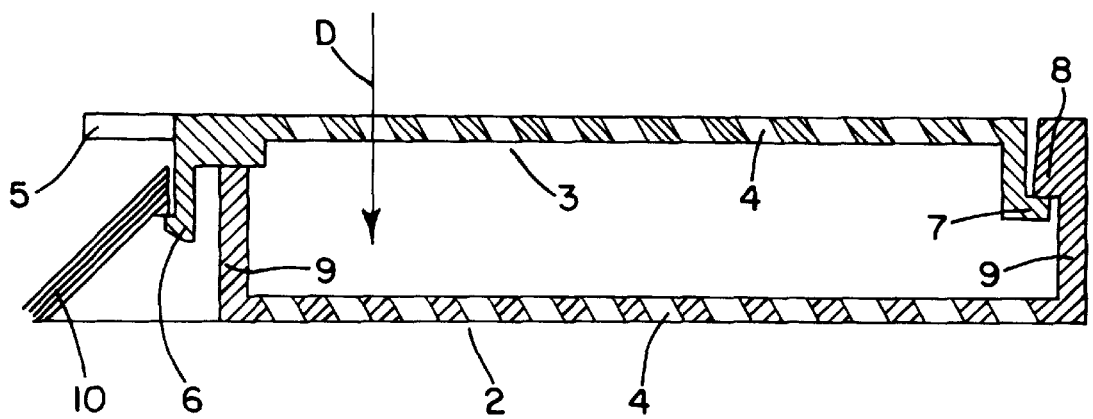
FIG. 2 shows a section through the closed cartridge along the line I-I In FIG. 1.

FIG. 2 shows a section along the line I-I (FIG. 1) through the cartridge 1, with the slot-shaped openings 4 disposed obliquely (i.e., at an angle other than a right angle) in the bottom part 2 and lid part 3. The side walls of the openings 4 are designed parallel to one another. The flow direction D of the liquid, which is not shown, is indicated by an arrow. It is clear from this representation that the positioning of the openings 4 in the bottom part 2 and the positioning of the openings 4 in the lid part 3 are arranged offset in relation to one another. In conjunction with the obliquely disposed openings 4, this measure has the result that the direct flow direction is interrupted and the desired swirling of the liquid is obtained inside the cartridge 1.

Figure 3A:
FIG. 3a shows an illustrative embodiment of the arrangement of the openings in the lid part of the cartridge.
Figure 3B:
FIG. 3b shows a further illustrative embodiment of the arrangement of the openings in the lid part of the cartridge.

FIGS. 3a and 3b show further illustrative embodiments of the invention, the slot-shaped openings 4 in the lid part 3 in FIG. 3a being arranged in alignment with the openings 4 in the bottom part 2 (FIG. 2) in the flow direction D.

In FIG. 3b, the openings 4 in the lid part 3 are oriented in another direction in relation to the openings 4 in the bottom part 2 (FIG. 2). This likewise leads to an improved swirling of the liquid inside the cartridge 1 by means of a reversal of the direction of swirling.

Figure 4B:
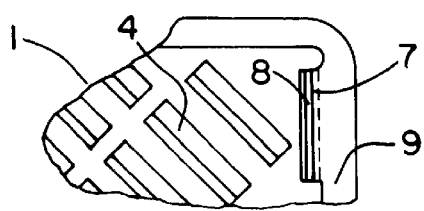
FIG. 4b shows a detail of the closed cartridge with a modified arrangement of the openings.
Figure 4A:
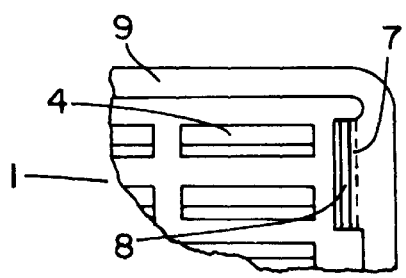
FIG. 4a shows a detail of the closed cartridge with an offset arrangement of the openings.

FIGS. 4a and 4b show further illustrative embodiments of the orientation of the openings 4 on the lid part 3 and bottom part 2, respectively. In these figures, the orientation of the individual openings 4 has been rotated in relation to the lateral parts 9. The angles of rotation in the lid part 3 can in this case differ from the angles in the bottom part 2.

It naturally falls within the scope of the invention to configure differently the orientation and dimensioning of the openings 4 on the lid part 3 and/or bottom part 2 and/or the direction of the openings 4 in the lid part 3 and/or the bottom part 2.

I claim:

1. A cartridge for treating samples in liquids, comprising:

a bottom part having a plurality of slot-shaped openings therethrough and a top surface;

solid lateral parts formed integrally with the bottom part; and a detachably secured lid part having a plurality of slot-shaped openings therethrough and a top surfaces, the slot-shaped openings in the bottom part and in the lid part being angled at other than a right angle relative to the top surface of the bottom part and the top surface of the lid part, respectively, and the slot-shaped openings in the bottom part being offset from the slot-shaped openings in the lid part in a direction perpendicular to a flow direction.

2. The cartridge according to claim 1, wherein an angle through the slot-shaped openings in the bottom part differs from an angle through the openings in the lid part.

3. The cartridge according to claim 1, wherein the longitudinal direction of at least one of the slot-shaped openings in the bottom part and the slot-shaped openings in the lid part is oriented at an oblique angle relative to the lateral parts.

4. The cartridge according to claim 1, wherein the bottom part and the lateral parts are comprised of a one-piece injection-molded plastic part.

* * * * *